(12) United States Patent
Martin-Villalba et al.

(10) Patent No.: US 7,935,339 B2
(45) Date of Patent: May 3, 2011

(54) INHIBITION OF THE CD95 LIGAND/RECEPTOR SYSTEM FOR THE TREATMENT OF NEUROLOGICAL DISORDERS AND INJURIES

(75) Inventors: Ana Martin-Villalba, Heidelberg (DE); Peter Krammer, Heidelberg (DE); Deana Demjen, Heidelberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 781 days.

(21) Appl. No.: 10/545,231

(22) PCT Filed: Feb. 10, 2004

(86) PCT No.: PCT/EP2004/001233
§ 371 (c)(1),
(2), (4) Date: Feb. 13, 2006

(87) PCT Pub. No.: WO2004/071528
PCT Pub. Date: Aug. 26, 2004

(65) Prior Publication Data
US 2006/0234968 A1    Oct. 19, 2006

(30) Foreign Application Priority Data
Feb. 14, 2003 (EP) ..................................... 03003426

(51) Int. Cl.
*A61K 39/395* (2006.01)
(52) U.S. Cl. ............... 424/130.1; 424/133.1; 424/178.1; 514/17.7
(58) Field of Classification Search .......................... None
See application file for complete search history.

(56) References Cited

U.S. PATENT DOCUMENTS 6,001,962 A * 12/1999 Ramer et al. ................. 530/324
2003/0082180 A1    5/2003 Krammer et al.
2003/0109416 A1    6/2003 Nagata et al.
2004/0014176 A1    1/2004 Ashkenzai et al.
2004/0053920 A1    3/2004 Bebbington et al.

FOREIGN PATENT DOCUMENTS

| EP | 0 842 948 | 5/1998 |
|----|-----------|--------|
| EP | 0 992 243 | 4/2000 |
| WO | WO 95/27735 | 10/1995 |
| WO | WO 99/14330 | 3/1999 |
| WO | WO 00/58466 | 10/2000 |
| WO | WO 01/41803 | 6/2001 |
| WO | WO 01/72707 | 10/2001 |

OTHER PUBLICATIONS

Martin-Villalba et al. Cell Death and Differentiation, vol. 8, 2001, pp. 679-686.*
Mehmet. Cell Death and Differentiation, vol. 8, 2001, pp. 659-661.*
Eves et al. J. Neurosci., vol. 21, 2001, pp. 4996-5006.*
Raoul et al. J. Cell Biology, vol. 147, 1999, pp. 1049-1061.*
Raoul et al. Current Opinion in Neurobiology, vol. 10, 2000, pp. 111-117.*
Martin-Villalba et al., J. Neurosci., vol. 19, 1999, pp. 3809-3817.*
Sakurai et al., Brain Res., vol. 797, 1998, pp. 23-28.*
M. Zurita et al: "Presence and Significance of CD-95 (FAS/AP01) Expression After Spinal Cord Injury." Journal of Neurosurgery, vol. 94; No. 2 suppl., Apr. 2001.
I. Herr et al: "Activation of CD95 (AP0-1/FAS) Signaling by Ceramide Mediates Cancer Therapy-Induced Apoptosis." The EMBO Journal, vol. 16, No. 20, Oct. 15, 1997.
D. Perez et al: "E1B 19K Inhibits FAS-Mediated Apoptosis Through FADD-Dependent Sequestration of Flice." The Journal of Cell Biology, vol. 141, No. 5, Jun. 1, 1998.
E. Bradbury et al: "Chondroitinase ABC Promotes Functional Recovery After Spinal Cord Injury." Nature, vol. 416, Apr. 11, 2002, pp. 636-640.

* cited by examiner

*Primary Examiner* — Jeffrey Stucker
*Assistant Examiner* — Stephen Gucker
(74) *Attorney, Agent, or Firm* — Millen, White, Zelano, Branigan, P.C.

(57) ABSTRACT

The present invention relates to the use of inhibitors of the CD95 ligand/receptor system for the manufacture of a medicament for the treatment of neurological disorders or injuries in a mammal, particularly for the treatment of spinal cord injury, more particularly for the treatment of paraplegia.

21 Claims, 6 Drawing Sheets

Fig. 5

Figure 1:
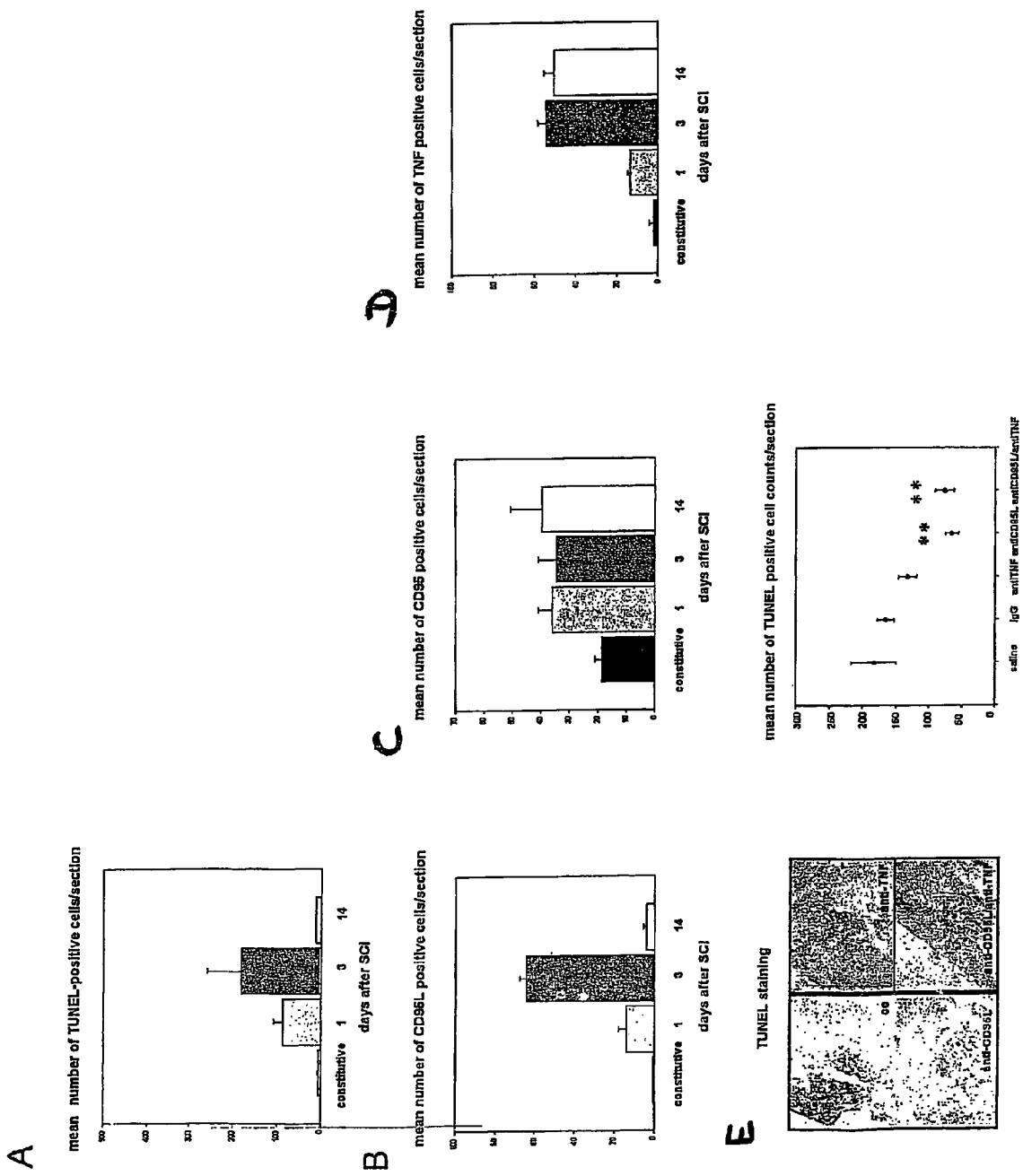

| Swimming score | | p-values |
|---|---|---|
| | | p≤0,05* |
| αCD95L vs. IgG | | p≤0,01** |
| | | p≤0,05* |
| | | p≤0,05* |
| | | p≤0,05* |
| αCD95L/αTNF vs. IgG | | p≤0,01** |
| | | p≤0,01** |
| | | p≤0,01** |

| Mechanical allodynia | | p-values |
|---|---|---|
| | | NS |
| αCD95L vs. IgG | | NS |
| | | NS |
| | | NS |
| | | p≤0,05* |
| αCD95L/αTNF vs. IgG | | p≤0,05* |
| | | p≤0,01** |
| | | p≤0,05* |

| Grid walk | | p-values |
|---|---|---|
| | | NS |
| αCD95L vs. IgG | | p≤0,05* |
| | | p≤0,01** |
| | | p≤0,01** |
| | | NS |
| αCD95L/αTNF vs. IgG | | NS |
| | | p≤0,01** |
| | | p≤0,01** |

| BBB score | | p-values |
|---|---|---|
| | | p≤0,01** |
| αCD95L vs. IgG | | p≤0,01** |
| | | p≤0,01** |
| | | p≤0,01** |
| | | p≤0,01** |
| αCD95L/αTNF vs. IgG | | p≤0,01** |
| | | p≤0,01** |
| | | p≤0,01** |

| Rotarod | | p-values |
|---|---|---|
| | | p≤0,01* |
| αCD95L vs. IgG | | NS |
| | | p≤0,01** |
| | | p≤0,01** |
| | | p≤0,01** |
| αCD95L/αTNF vs. IgG | | NS |
| | | p≤0,01** |
| | | p≤0,01** |

INHIBITION OF THE CD95 LIGAND/RECEPTOR SYSTEM FOR THE TREATMENT OF NEUROLOGICAL DISORDERS AND INJURIES

The present invention relates to the use of inhibitors of the CD95 ligand/receptor system for the manufacture of a medicament for the treatment of neurological disorders or injuries in a mammal, particularly for the treatment of cerebral or spinal cord injury, more particularly for the treatment of paraplegia.

Apoptotic cell death contributes to secondary damage and neurological dysfunction following spinal cord injury (SCI) (1). Main inducers of the apoptotic program in other neurodegenerative models, such as stroke (2), are the TNF- and CD95-ligand/receptor systems. Tumor necrosis factor-receptor-1 (TNF-R1, p55, CD120$a$) and CD95 (APO-1, Fas), like other death receptors, are characterized by the presence of a death domain which is crucial for the transduction of the apoptotic signal (3). Ligation of receptors by trimerized ligands leads to the recruitment of the adapter protein FADD (Fas-associated death domain, MORT1; (4) and caspase-8 into a death inducing signaling complex (DISC) (5). Caspase-8 at the DISC is activated through self-cleavage (6), and commits the cell to apoptosis by activation of downstream effector caspases.

Activation and cleavage of both caspase-1 and caspase-3 were detected in neurons following SCI, and their inhibition reduces post-traumatic lesion size (7). Following SCI, expression of TNF, CD95 and CD95L is increased at the lesion site (8). The role of TNF-L/R system in SCI in vivo, however, is controversial. On the one hand, neutralization of TNF significantly reduced the number of apoptotic cells following SCI (9). On the other hand, in mice lacking TNF or TNF-R1 more apoptotic cells could be identified, the lesions were larger, and they displayed worse functional recovery than wild-type (wt) mice (10). Expression of CD95 was found in astrocytes, oligodendrocytes, and microglia following cervical SCI (11). However, the implication of the CD95-L/R system in SCI remains to be elucidated, even though WO 01/41803 suggests the use of combinations of TNFa and CD95L inhibitors for the prevention or treatment of degenerative disorders, e.g. Alzheimer, Parkinson and spinal cord damages.

WO 99/14330 discloses the DcR3 polypeptide, a TNFR homologue. The DcR3 polypeptide or a chimeric molecule comprising the DcR3 polypeptide is capable of inhibiting CD95L-induced apoptosis in mammalian cells. There is, however, no data which demonstrates that an inhibition of the CD95-system is beneficial for the treatment of SCI.

In (42) the expression of CD95 in a rat SCI model is assessed by immunohistochemistry with a monoclonal antibody directed against CD95. Immunoreactivity with CD95 is detected in the white and grey matter (in astrocytes, oligodendrocytes and neurons) up to two weeks post-injury. According to the authors, the detection of CD95-positive cells suggests that blocking of the CD95 system might be a plausible therapeutic approach for SCI.

The data in (42), however, do not allow the conclusion that an inhibition of the CD95 is in fact beneficial for the treatment of SCI. Cellular expression of the CD95 is necessary but not sufficient for the induction of apoptosis through the CD95-system. For example, astrocytes, one of the cell types which according to (42) express CD95, are not susceptible to CD95-mediated apoptosis (43). Thus the mere detection of CD95 does not allow the conclusion that this system is involved in the induction of death of these cells. Along this line, the lack of expression of the TNF receptor (10 and 44), which is also involved in apoptosis, does not result in a better clinical outcome following SCI. Thus, any conclusion drawn to the efficacy of a potential treatment against SCI has to be supported by functional data. As a resume: (42) shows merely descriptive data that does not allow the conclusion that the CD95-system is involved in SCI-induced damage.

In the present application, we show for the first time functional data which allow the conclusion that inhibition of the CD95-system significantly improves the clinical outcome after spinal cord injury. Thus, the present application is the first enabling disclosure for the treatment of SCI by inhibitors of the CD95-system.

To address whether the CD95- and the TNF-ligand/receptor (L/R) systems are involved in SCI-induced damage, a rodent model of SCI was used. Following dorsal transection of the spinal cord, the expression of CD95, CD95L and TNF increased at the site of the injury. Therapeutic neutralization of CD95L alone or of both CD95L and TNF decreased apoptotic cell death following SCI. Most importantly, mice treated with anti-CD95L-antibodies, anti-CD95L/anti-TNF-antibodies or with CD95-Fc fusion proteins were capable of initiating active movements which was not the case for mice in control groups or treated with anti-TNF alone. The improvement in the locomotor performance in animals lacking CD95L activity was mirrored by an increase in the regenerating fibers at the site of the lesion and a parallel upregulation of the growth associated protein-43. Moreover, neutralization of the CD95L/R system increased expression of the myelin basic protein, an indirect marker of oligodendrocyte viability, and of the neuronal marker, βIII-tubulin. Here we demonstrate for the first time that neutralization of CD95L promotes axonal regeneration in the adult injured spinal cord and functional improvement of injured animals.

A first aspect of the invention relates to the use of inhibitors of the CD95L/R system for the manufacture of a medicament for the treatment of cerebral or spinal cord injury, e.g. cerebral lesions or partial or complete spinal cord lesions, particularly paraplegia in a mammal, e.g. in a human patient. Surprisingly, it was found that spinal cord injuries, e.g. lesions in adult subjects may be successfully treated. Further, it was found that the invention is particularly useful for the treatment of acute injuries. The injury, particularly the spinal cord injury may be caused by a cut, a compression, by an ischemic condition or by other means. The administration of CD95L/R inhibitors leads to a functional recovery comprising an improved axon growth, particularly a growth of neurons, microglia and/or oligodendrocytes. Especially preferred indications are the regeneration of locomotor performance, the improvement of stimulation and/or the recovery of movement coordination after spinal cord injury.

In a preferred embodiment of the invention, the inhibitor is a CD95-ligand (Fas ligand; APO1 ligand) inhibitor. For example, CD95-ligand inhibitors may be selected from (a) an inhibitory anti-CD95 ligand-antibody or a fragment thereof;
(b) a soluble CD95 receptor molecule or a CD95 ligand-binding portion thereof; and
(c) a Fas ligand inhibitor selected from FLINT, DcR3 or fragments thereof.

Preferred are inhibitory anti-CD95L-antibodies and antigen-binding fragments thereof and soluble CD95R molecules or CD95L-binding portions thereof. Examples of suitable inhibitory anti-CD95L antibodies are disclosed in EP-A-0 842 948, WO 96/29350, (38), WO 95/13293 or (39) as well as chimeric or humanized antibodies obtained therefrom, cf. e.g. WO 98/10070. Further preferred are soluble CD95 receptor molecules, e.g. a soluble CD95 receptor molecule without transmembrane domain as described in EP-A-0 595 659 and EP-A-0 965 637 or CD95R peptides as described in WO 99/65935, which are herein incorporated by reference.

Especially preferred is a CD95L inhibitor which comprises an extracellular domain of the CD95R molecule (particularly amino acids 1 to 172 (MLG . . . SRS) of the mature CD95 sequence according to U.S. Pat. No. 5,891,434) optionally fused to a heterologous polypeptide domain, particularly a Fc immunoglobulin molecule including the hinge region e.g. from the human IgG1 molecule. A particularly preferred fusion protein comprising an extracellular CD95 domain and a human Fc domain is described in WO 95/27735, which is herein incorporated by reference.

The Fas ligand inhibitor FLINT or DcR3 or a fragment, e.g. soluble fragment thereof, for example the extracellular domain optionally fused to a heterologous polypeptide, particularly a Fc immunoglobulin molecule is described in WO 99/14330, WO 99/50413 or (41) which are herein incorporated by reference. FLINT and DcR3 are proteins which are capable of binding the CD95 ligand and LIGHT, another member of the TNF family.

In a further embodiment of the present invention, the inhibitor is a CD95R inhibitor which may be selected from
(a) an inhibitory anti-CD95 receptor-antibody or a fragment thereof; and
(b) an inhibitory CD95 ligand fragment.

Examples of suitable inhibitory anti-CD95R-antibodies and inhibitory CD95L fragments are described in EP-A-0 842 948 and EP-A-0 862 919 which are herein incorporated by reference.

In still a further embodiment of the present invention the inhibitor is a nucleic acid effector molecule. The nucleic acid effector molecule may be selected from antisense molecules, RNAi molecules and ribozymes which are capable of inhibiting the expression of the CD95R and/or CD95L gene.

In a still further embodiment the inhibitor may be directed against the intracellular CD95R signal transduction. Examples of such inhibitors are described in WO 95/27735 e.g. an inhibitor of the interleukin 1β converting enzyme (ICE), particularly 3,4-dichloroisocoumarin, YVAD-CHO, an ICE-specific tetrapeptide, CrmA or usurpin (WO 00/03023). Further, nucleic acid effector molecules directed against ICE may be used.

The inhibitor or a combination of the above inhibitors is administered to a subject in need thereof, particularly a human patient, in a sufficient dose for the treatment of the specific condition by suitable means. For example, the inhibitor may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e.g. intraperitoneally, or intravenously, or locally, e.g. intrathecally or by lumbar puncture. Preferred is an intrathecal administration.

The pharmaceutical composition is preferably administered in the case of acute injuries. Alternatively, the invention encompasses a treatment of non-acute injuries, wherein a new damage is introduced, e.g. by an incision or a cut and the recently introduced damage is subjected to a CD95R/L inhibitor treatment. More preferably, the treatment is started as soon as possible, e.g. immediately after the occurence of spinal cord injury, and continued for a sufficient time, e.g. up to 30 days. The composition may be administered once or several times, e.g. once a day, several times a day, each second day etc.

In some embodiments of the present invention the medicament may comprise a further active ingredient. The further active ingredient may be selected from apoptosis inhibitors, particularly intracellular apoptosis inhibitors, e.g. caspase inhibitors such as caspase-3 or caspase-8 inhibitors, Bid inhibitors, Bax inhibitors or any combination thereof. Examples of suitable inhibitors are caspase inhibitors in general, cf. WO 02/094263, WO 01/10383, WO 01/42216, WO 01/90070, WO 01/94351, WO 01/21600, WO 00/61542, WO 99/47545, dipeptide inhibitors (WO 99/47154), carbamate inhibitors (WO 01/72707), substituted aspartic acid acetals (WO 01/81330), heterocyclyidicarbamides (WO 02/085899), quinoline-(di-, tri-, tetrapeptide) derivatives (US 200126467), substituted 2-aminobenzamide caspase inhibitors (WO 00/55114), substituted a-hydroxy acid caspase inhibitors (WO 01/16093) inhibition by nitrosylation (WO 98/43621); CASP-1: (WO 02/000853; CASP-3: protein-inhibitors (WO 02/066050), antisense molecules (WO 01/53310), nicotinyl-aspartyl-ketones (WO 01/27085), y-ketoacid dipeptide derivatives (WO 02/48179, WO 00/32620, WO 00/55127), CASP-8: antisense molecules (WO 01/53541), interacting proteins (WO 00/39160) CASP-9: antisense modulators (WO 02/22641); CASP2: antisense molecules (WO 02/24720); CASP-6: antisense molecules (WO 02/29066); CASP-7: antisense molecules (WO 02/22640); CASP-12 inhibitors: WO 00/59924, which are herein incorporated by reference. Further examples are mitochondrial inhibitors such as Bcl-2-modulating factor (WO 02/097094); Bcl-2 (WO 94/27426) mutant peptides derived from Bad (WO 02/20568), Bad (WO 96/13614), BH3-interacting domain death agonist (WO 98/09980), Bax inhibitor proteins (WO 98/40397), BLK genes and gene products (WO 99/50414) which are herein incorporated by reference. Further suitable intracellular modulators of apoptosis are modulators of CASP9/Apaf-1 association (WO 02/064128), antisense modulators of Apaf-1 expression (WO 02/32921), peptides for inhibition of apoptosis (WO 99/43701), antiapoptotic compositions comprising the R1 subunit of Herpes Simplex virus (WO 00/07618), MEKK1 and fragments thereof (WO 99/41385), modulators of Survivin (WO 01/64741), modulators of inhibitors of apoptosis (WO 97/06182, WO 00/77201, WO 01/59108, WO 02/053586) and HIAP2 (WO 00/08144) which are herein incorporated by reference. Further, any combination of the above inhibitors may be used.

The further ingredient may also be selected from inhibitors of death ligand receptor systems (other than CD95L/R) such as the TRAIL-L/TRAIL-R System (cf. WO 98/35986), the TRAMP-R/TRAMP-R system or the DR6-L/DR6-R system (cf. U.S. Pat. No. 6,423,494 or WO 01/85209 or the TNF/TNF-R system. Suitable inhibitors are inhibitory anti-death ligand or receptor antibodies or antigen-binding fragments thereof or soluble death receptor molecules or death ligand-binding portions thereof, e.g. fusions with Fc immunoglobulin domains.

For example, the further active ingredient may be selected from inhibitors of the TNF L/R system, e.g. an inhibitory anti-TNF antibody or a fragment thereof as described in WO 95/20978, WO 96/33204 or WO 02/012502, a soluble TNF receptor molecule optionally fused to a heterologous polypeptide domain, particularly an Fc immunoglobulin domain as described in WO 98/24463 or a TNF binding protein as described in WO 96/03141, herein incorporated by reference. The administration of a TNF L/R inhibitor is particularly suitable for the attenuation of hyperalgesia.

A combined administration of CD95L/R inhibitors and TNF L/R inhibitors is disclosed for example in WO 01/41803 which is herein incorporated by reference.

Preferably however, the CD95L/R inhibitor is administered without TNF L/R inhibitor. By this means, the occurrence of potential detrimental side-effects can be reduced or eliminated, since an inhibition of TNF did cause severe complications in several mouse models, e.g. cecal ligation and puncture (40).

Additional examples of further active ingredients are compounds which inhibit the formation of glial scars, such as chondroitinase ABC.

The dose of the inhibitor administered will of course, be dependent on the subject to be treated, on the subject's weight, the type and severity of the injury, the manner of administration and the judgement of the prescribing physician. For the administration of anti-CD95R or L-antibodies or soluble CD95R proteins, e.g. CD95-Fc fusion proteins, a daily dose of 0.001 to 100 mg/kg is suitable.

The present invention is further illustrated by the following Figures and Examples.

FIG. 1 Apoptotic cell death peaks at 3 days after SCI and is significantly decreased by treatment with anti-CD95L antibody.

(A) Apoptotic cell death was assessed by TUNEL staining in sham-operated animals and at 1-, 3- and 14 days after thoracic SCI in wt C57BL/6 animals (n=4 per group). (B) CD95L-positive cell counts; (C) CD95-positive cell counts; (D) Number of TNF-positive cells. Cells were counted in three 20 µm thick spinal cord sections 200 µm away from each other in sham-operated animals and 1, 3 and 14 days following SCI (n=4 mice per group). (E) Wt animals subjected to SCI were i.p. treated either with anti-CD95L, anti-TNF, or anti-CD95L/anti-TNF, or with saline or IgG as a control (n=4 per group). After a survival time of 3 days, apoptotic cells stained by TUNEL and were counted in three 20 µm sections 200 µm away from each other. Data are presented as mean±S.E.M. The significance was determined by comparing the number of apoptotic cells in antibody-treated animals to the control groups, using the Wilcoxon Rank Sum Test (**p≦0.01).

Figure 2:
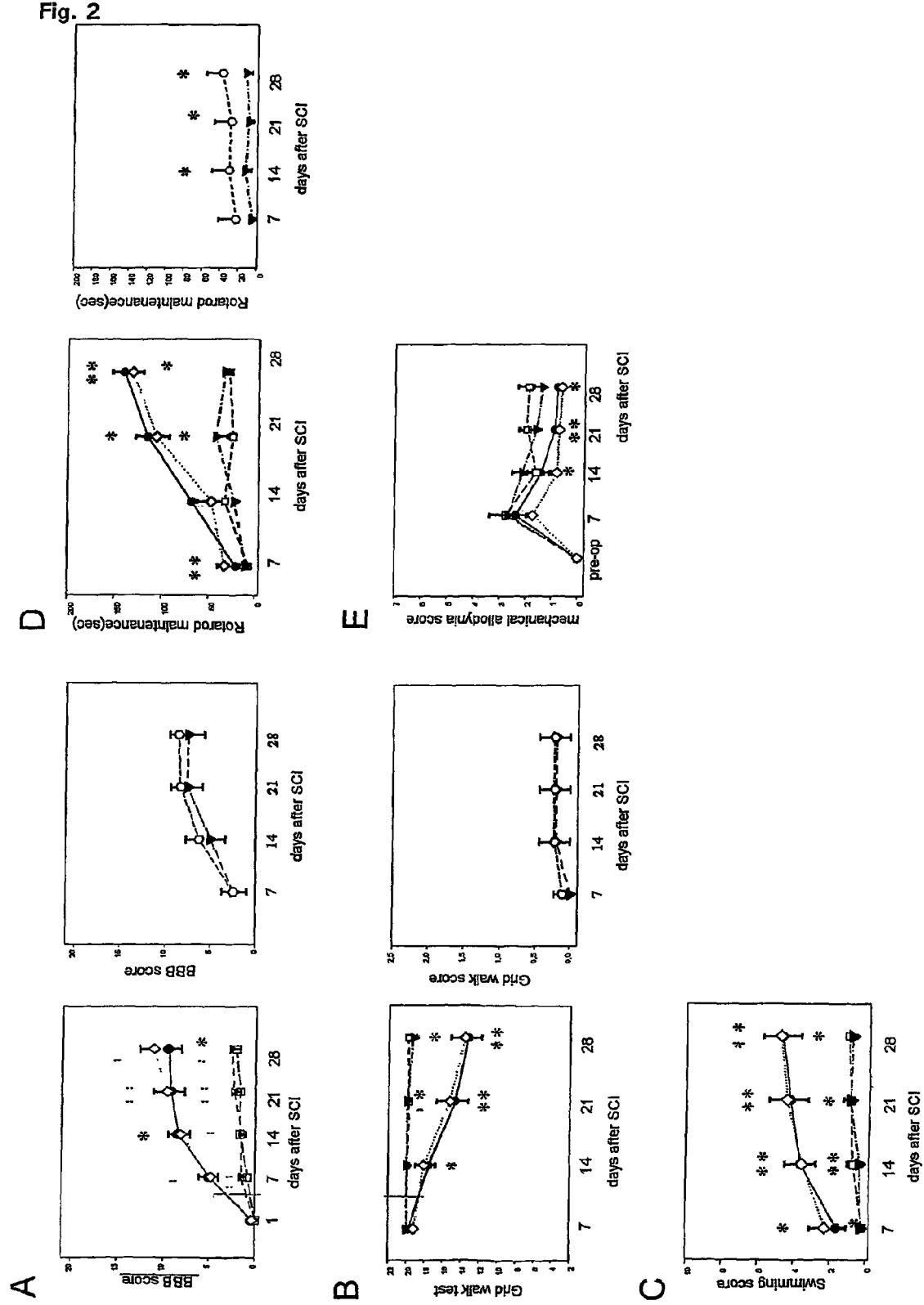

FIG. 2 Functional recovery after SCI is improved in animals having a block of CD95L or CD95L and TNF.

Animals were treated either with anti-CD95L (black circles) or anti-CD95L/anti-TNF-antibodies (open diamonds), or with saline (black triangles) or IgG (open squares) as a control (n=11 per group). In a second set of experiments, animals were treated with anti-TNF antibody (open hexagons) or saline (black triangles) as control. All behavioural tests were performed in a double blind manner. Animals were tested at 1, 2, 3 and 4 weeks after the injury in the following tasks: (A) BBB (for this, animals were additionally tested at day one after SCI); (B) grid walk; (C) swimming performance; (D) maintenance time on the rotarod; (E) reaction to mechanical stimulation by "von Frey hairs". For all the tasks tested, there were no significant differences between the two control groups, nor between the two treated groups at any of the time points studied. Data are presented as mean±S.E.M. Only p-values comparing anti-CD95L- and anti-CD95L/anti-TNF-treated groups to the saline group are shown in the graphs; p-values comparing treated groups to IgG group are given in the FIG. S1; (* p≦0.05; ** p≦0.01 Wilcoxon Rank Sum Test).

Figure 3:
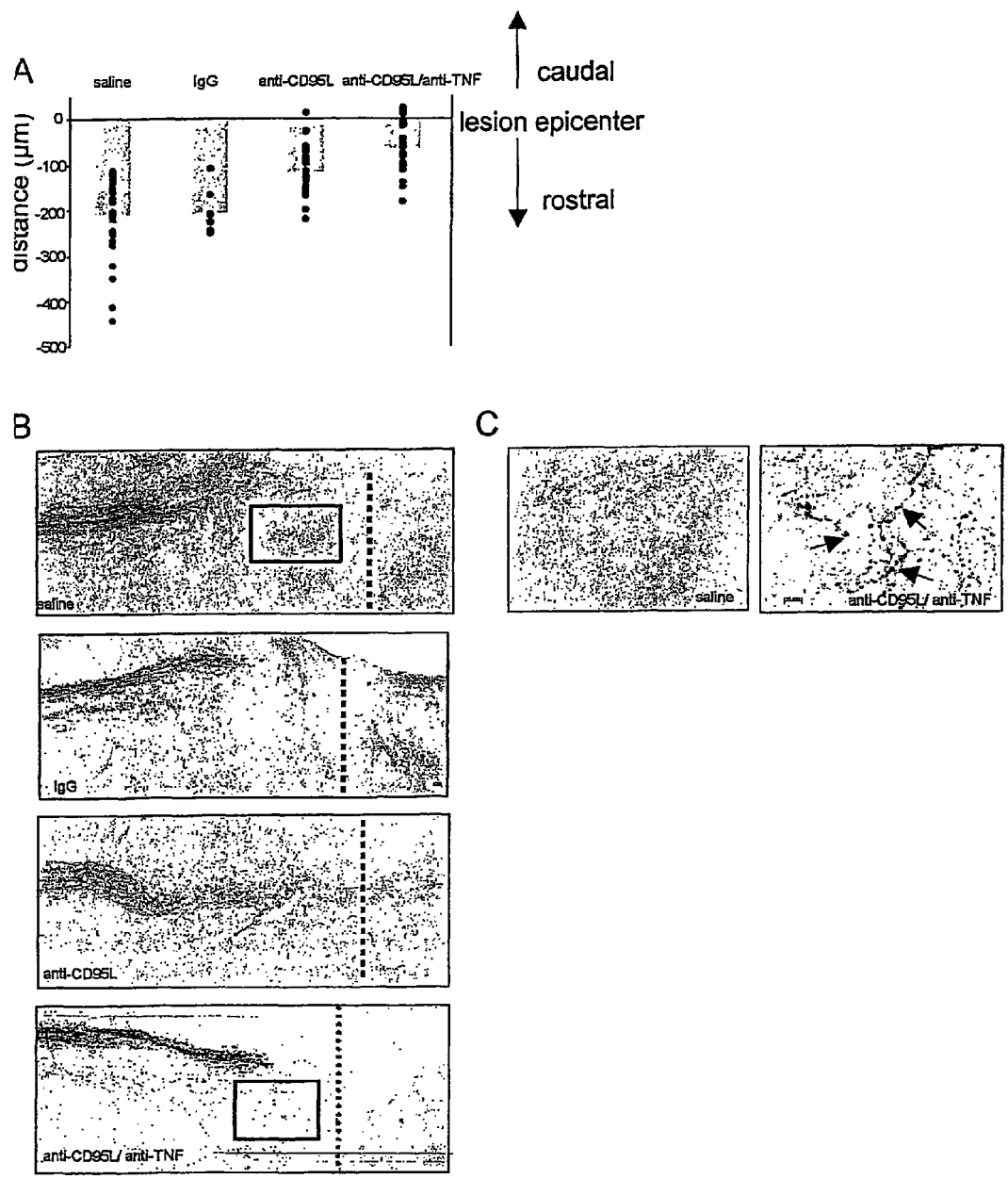

FIG. 3 Regeneration of corticospinal tract (CST) in anti-CD95L and anti-CD95L/anti-TNF treated animals after SCI.

Biotin dextran amine (BDA) was injected into the sensory-motor cortex (coordinates: Bregma −1.5; 1; 1) of the anti-CD95L-, anti-CD95L/anti-TNF-, saline, and IgG-treated animals two weeks after SCI (n=4-5 per group). (A) At 4 weeks postinjury, the distance from the epicenter of the lesion to the most caudally extending regenerating fibers was determined in three consecutive spinal cord sections. Anterogradely labeled fibers retract from the lesion site in saline- and IgG-treated animals by 250±11.5 µm. The mean distance to the epicenter of the lesion in antibody-treated animals is markedly less (95±62 µm). (B) Examples of BDA-labeled corticospinal fibers in representatives for each group. The epicenter of the lesion is indicated by a vertical line. The CST retracts from the lesion site in saline- and IgG-treated control animals (upper panels), whereas numerous ectopic fibers sprouting from the transected CST grow into the dorsal white matter and lesion scar in anti-CD95L- and anti-CD95L/anti-TNF-treated animals (lower panels). (C) Higher magnification of framed regions shows regenerative sprouting and synaptic buttons rostral to the lesion site in anti-CD95L/anti-TNF-treated animals (right box), or no regenerative sprouts in the corresponding region in saline-treated animals (left box). Scale bar, 20 µm; framed regions, 10 µm.

Figure 4:
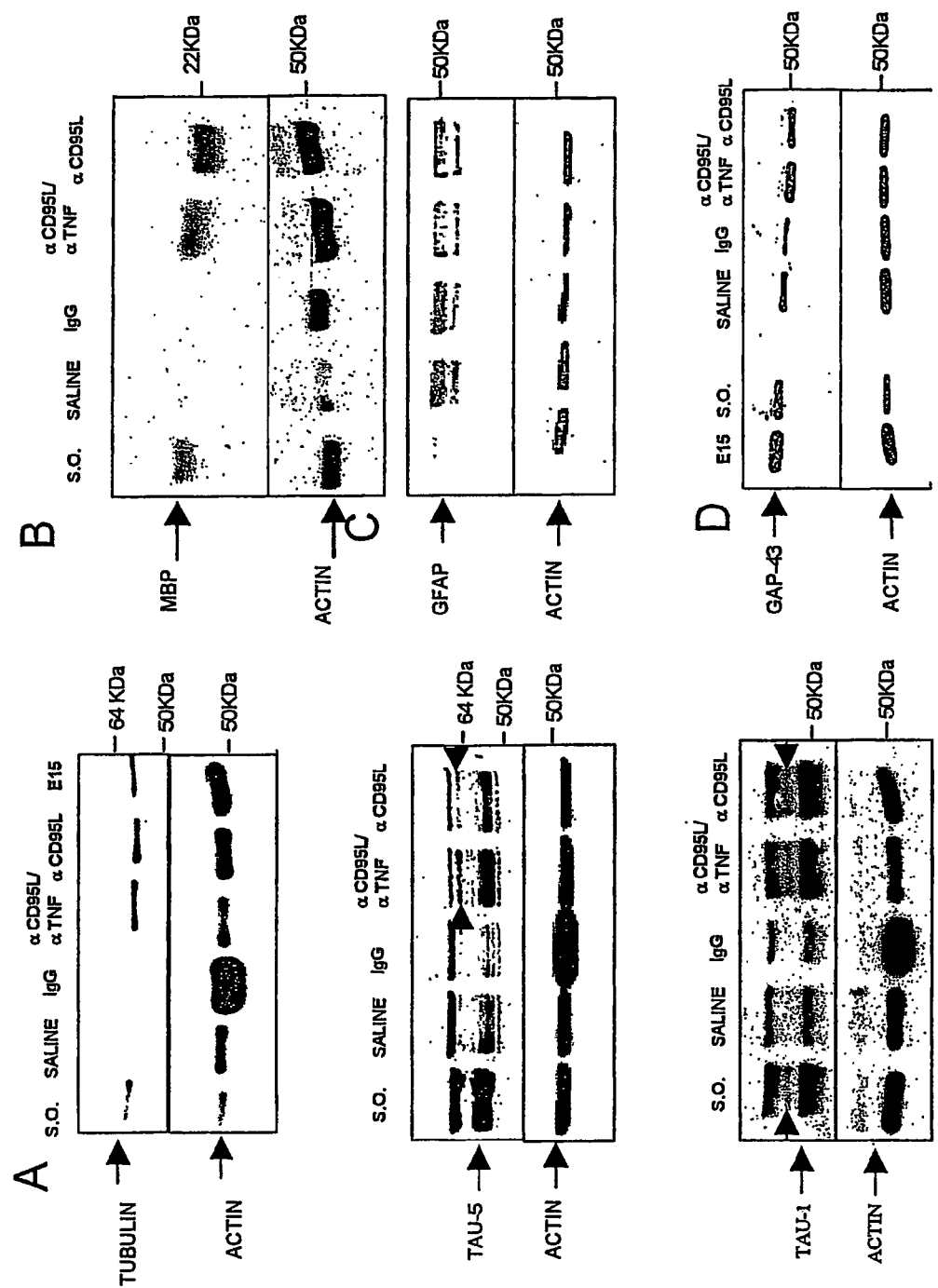

FIG. 4 Reduced secondary damage and enhanced regeneration in anti-CD95L and anti-CD95L/anti-TNF treated animals.

Animals were subjected to SCI and treated either with anti-CD95L alone or together with anti-TNF antibody, or with saline or IgG as a control. After survival time of 4 weeks, the indicated proteins were detected by Western blot analysis (n=3 per group). Actin was used as a control for equal protein loading (20 µg) in each lane. (A) Analysis of expression levels of neuronal markers in antibody- and control-treated animals, shown as the specific bands of 50 kDa for βIII-Tubulin-, Tau-5-, and Tau-1-proteins; (B) 22 kDa band for MBP; (C) 50 kDa band for GFAP; (D) 43 kDa band for GAP-43. S.O.=sham-operated; E15=embrional day 15.

FIG. 5 Statistical analysis of behavioural tests data for mice in the anti-CD95L- and anti-CD95L/anti-TNF-treated groups vs. IgG-treated group.

p-values comparing anti-CD95L- and anti-CD95L/anti-TNF-treated groups to IgG group for every test are shown (Wilcoxon Rank Sum Test); * p≦0.05; ** p≦0.01 for all the tests, NS=not significant.

Figure 6:
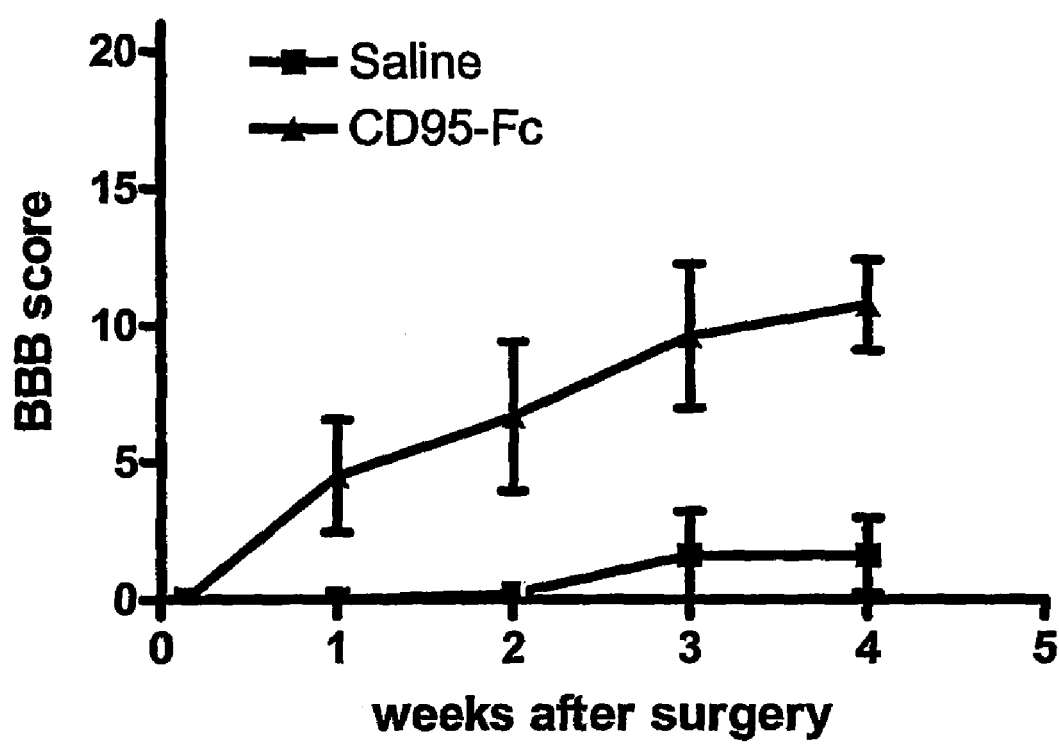

FIG. 6 Functional recovery after SCI is improved by administration of CD95-FC-Fusion protein.

Animals were treated either with CD95-Fc (black triangles) or with saline (black squares) as a control. Animals were tested at one, two, three and four weeks after the injury in the BBB-task.

TABLE 1

Swimming Score

Swimming performance of the animals was evaluated by scoring the following features: hindlimb movements, hindlimb-forelimb coordination, tail position, paw position, saggital and coronal balance.

EXAMPLE 1

Treatment of SCI with an Anti-CD95L Antibody

1. Materials and Methods
1.1 Spinal Cord Injury Model

Spinal cord injury was performed in female wild-type (wt) mice on a C57BL/6 background, all matched for age (mean 75 days) and weight mean 24 g). Deep anesthesia was reached by the i.p. injection of Ketamin and Rompun (150 mg/kg body weight each). The laminectomy on vertebral level Th8/9 was performed in order to expose the spinal cord. The dorsal spinal cord was symmetrically lesioned with fine irridectomy scissors (FST, Heidelberg), resulting in a two-thirds section that left only the fibers in ventral funiculus intact. After suturing the muscles and the skin separately, the mice were allowed to recover on the heating block (37° C.) before being returned to the cages.

The animals were postoperatively treated with antibiotics, (Gentamycin, 5 ml/kg at 0.2 mg/ml) once a day for seven days. All mice were kept in 12 hr light/dark cycle and received water and food ad libitum. Their bladders were manually expressed once a day until restoration of autonomic bladder function.

The animals were subjected to SCI, and after different survival times (1, 3, and 14 days), they were deeply anesthetized and killed by intracardial perfusion.

For antibody treatment, either anti-CD95L antibody (MFL3; Pharmingen, Germany) alone, or together with anti-TNF antibody V1q, (32) 50 µg each, were used. The antibodies were i.p. injected either 30 min after the lesioning and every day for up to 3 days (survival time 3 days, n=4 per group), or 2 h before the injury twice a week up to four weeks (survival time 4 weeks, n=11 per group), in a double blind manner. In addition, the mice were injected with saline and rat IgG (Sigma) as a control. In a second series of experiments mice were i.p. treated with anti-TNF antibody alone or saline as a control. After survival times of either 3 days or 4 weeks, mice were deeply anesthetized and killed by intracardial perfusion or decapitation.

1.2 Terminal Deoxynucleotidyl Transferase-Mediated Biotinylated UTP Nick End Labeling (TUNEL)

Longitudinal cryostat spinal cord sections (20 µm) were processed according to the terminal deoxynucleotydil transferase (TdT)-mediated biotinylated UTP nick end-labeling (TUNEL) technique (33). Nuclei were stripped from proteins by incubation in PBS with 1% TritonX-100 at 4° C. overnight. Endogenous peroxidase was inactivated by covering the sections with 2% $H_2O_2$ for 5 min at room temperature. Sections were incubated with 0.35 mM biotinylated dUTP, 10 units TdT buffer, 2 mM $CoCl_2$, 1 mM dATP (Roche, Switzerland), in a moist chamber at 37° C. for 60 min. The reaction was terminated by transferring the slides to Tris-EDTA buffer at room temperature for 15 min. The sections were further processed using the avidin-biotin-complex (ABC) system (Vector laboratories) and subsequent diamiobenzidine (DAB; Sigma) incubation. Normal nuclei, which contained only an insignificant amount of DNA 3'-OH ends, did not stain with this technique. Cells with necrotic morphology and detectable concentrations of DNA ends showed a more diffuse labeling compared with the apoptotic nuclei. As a control, sections were incubated in the absence of either the enzyme or the nucleotide. Apoptotic cells were counted in three consecutive sections 200 µm away from each other in 4 mice/group by a person blinded to the treatment. All data are given as mean±S.E.M. Significance was measured using the Wilcoxon test.

1.3 Immunohistochemistry and Immunofluorescence

Longitudinal cryostat spinal cord sections (20 µm) from untreated mice were processed for immunohistochemistry and immunofluorescence. After survival time of 1, 3 or 14 days, the sections were incubated with primary antibodies against CD95L, CD95 (M20, Santa Cruz) and TNF-a (Sigma). Immunoreactivity of CD95L, CD95 and TNF-a proteins was visualized by diaminobenzidine (Alexis, Germany). Only CD95 was detectable in the spinal cords of sham-operated animals, whereas all of them were detectable in the mouse thymus and in sections from tumors transfected with murine CD95L. Neither of these three proteins could be detected in control stainings performed without the first antibody or isotype control IgG. Double immunofluorescence was performed with previous primary antibodies, and the neuronal-(NeuN, Chemicon), lymphocyte-(CD3, Chemicon), astrocyte-(GFAP, Chemicon), oligodendrocyte-(oligodendrocyte marker, Chemicon), and microglial-(CD11b, Serotec) marker. Immunoreactivities were visualized with either a mono- or a polyclonal Cy3- and FITC-labeled secondary antibody (Dianova, Hamburg, Germany). To test the distribution of the MFL3 antibody in the spinal cord, biotynilated MFL3 antibody (Pharmingen, Germany) was used. The antibody was i.p. injected 2 h before SCI, and after survival times of 3-, 6- or 24 h, the longitudinal spinal cord sections were processed for streptavidin-rhodamine staining (Dianova, Germany).

1.4 Anterograde Tracing of Corticospinal Tract (CST)

Two weeks after the spinal cord lesioning, some of the animals (n=5 per group) were deeply anesthetized and placed in the stereotactic frame. The scalp was incised and holes were drilled into the sensorimotor cortex. Pressure injections of 1 µl of a 10% solution of biotinylated dextran-amine (BDA, Molecular Probes, Eugene, Oreg.) in saline, were made bilaterally into the sensory-motor cortex (coordinates: Bregma −1.5; 1; 1). Two weeks after the injection, free floating spinal cord sections (50 µm) were processed for BDA staining, as described previously (34). The only clear reference point at the lesion site was the lesion epicenter. Therefore, we quantified the distance from the caudalmost sprout to the lesion epicenter (Scion Image, Scion.comp). The distance beyond the epicenter of the lesion was scored as positive-, and otherwise negative distance.

1.5 Western Blot

Spinal cord tissue from the lesion site (1 mm both rostral and caudal to the lesion) of 3 animals per group was lysed in RIPA buffer (150 mM NaCl, EDTA 1 mM, Na-deoxycholate 0.5%, NP-40 1%, Tris-HCl 50 mM pH 7.4, supplemented with protease inhibitors PMSF 1 mM, aprotinin, leupeptin and pepstatin 1 µg/ml each), and sonicated. The following monoclonal antibodies were used: mouse anti-tubulin (1:2000, Chemicon), mouse tau Ab-2 (Clone TAU-5, 1:2500, Neomarkers), mouse anti-tau-1 (1:2500, Chemicon), rat anti-myelin basic protein (MBP, 1:8000, Chemicon), mouse anti-glial fibrillary acidic protein (GFAP, 1:2500, Chemicon), and mouse anti-growth associated protein-43 (GAP-43, 1:2500, Sigma). Bound antibodies were detected with either anti-mouse or anti-rat horseradish peroxidase conjugate (1:5000, Amersham) and enhanced chemiluminescence (Nalgene). Tissue from individual animals was analyzed separately. For alkaline phosphatase treatment, protein lysates were incubated with 50 mM Tris pH 8.5, 0.1 mM EDTA and protease inhibitor 3 h at 37° C., and then 0.25 U alkaline phosphatase/µg protein was added.

1.6 Cell Culture

The hippocampi of E15 mice were dissected, trypsinized, and physically dissociated. The cells were then washed in HBSS, and 300.000 cells were plated onto poly-L-lysine (PLL) glass coverslips in 6 cm Petri dishes containing minimal essential medium (MEM) and 10% inactivated horse serum. The cells were kept in 5% $CO_2$ at 36.5° C. for 4 hr. The coverslips were then transferred to the MEM containing B-27 and N2 supplement. After 8 days in vitro (DIV), cultured hippocampal neurons were subjected to axotomy (Laser Palm), and immediately treated with either 10 µg/ml anti-CD95L, or 10 µg/ml IgG for 24 h, or left untreated.

The cells were then fixed in 4% PFA in PBS, washed, and stained with GAP-43 antibody (GAP-43, 1:250, Sigma). Immunoreactivity was visualized with a monoclonal rhodamin labeled secondary antibody (Dianova, Hamburg, Germany). In order to visualize apoptotic nuclei, DAPI (1:1000, Sigma) was added into the secondary antibody.

1.7 Behavioural Testing

All behavioural tests were performed in a double blind manner. Animals were tested at 1, 2, 3 and 4 weeks after injury. For BBB score, animals were additionally tested at day one after SCI. The animals were monitored with video-camera while testing, and their performance was evaluated from digitized videos at one-fourth speed.

BBB Locomotor Score

Overall locomotor performance of the animals was assessed using the BBB locomotor rating scale with slight modifications (35). The mice were placed on a plexiglas runway of 1 m length and 6 cm width. The runway was placed on top of an inclined mirror (60° angle), to facilitate the observation of the hind-limb movements. Each animal had to cross the runway three times. In each testing session, the animals were assigned points independently by two observers blinded to the treatment. The hindlimb locomotion was scored from 0—(for no observable hindlimb movement) to 21 points. The scale was modified if the sequence of recovering motor features was not the same as described in original score. Since mice raise their tails early in their recovery (already at score of 10 points), additional 0.5 points were given for the tail position.

Grid Walk Test

Deficits in descending motor control were examined by assessing the ability to navigate across a 1 m long runway with irregularly assigned gaps (0.5-2 cm) between round metal bars (36). A defined 10 bar sector was chosen for the analysis. To prevent habituation to a fixed bar distance, the bars in this sector were changed for each testing session. Each animal had to cross this sector three times. Analysis was performed by counting the number of errors in foot placing: if the animal did not have hindlimb weight support, it would make 2 errors per bar, resulting in a total of 20 errors.

Swimming Score

In order to obtain information about locomotor performance in the absence of the cutaneous and proprioceptive input from the limbs to the spinal cord, we used a swimming test. Mice were allowed to swim in a tank 1 m long and 6 cm wide at which end they could climb out of the water to an island (with either 45° or 60° slope). Time used for swimming and climbing did not reflect the degree of performance of the animals, since it was much influenced by the motivation of the animals to cross the tank, which could not be standardized by training or offering a reward at the end of each performance. Therefore, we evaluated the swimming performance by scoring the following features: hindlimb movements, hindlimb-forelimb coordination, tail position, paw position, saggital and coronal balance. Each animal had to cross the tank twice and was assigned points in each testing session.

Rotarod Test

To test a motor coordination and skill learning, rotarod test was performed. The animals were placed on a plastic roller (5 cm diameter, 10 cm length and 40 cm above ground), which was accelerated for 20 sec (from 4-7 r.p.m.). The maintenance time was recorded for up to 180 sec, in three trials for each animal.

Mechanical Allodynia Test

To assess the nociceptive behavior of the animals, we performed a "von Frey hair" test for mechanical allodynia. The animals were put inside a metal cylinder with round holes in order to introduce "von Frey hairs". Mice were tested for responses to mechanical stimulation with "von Frey hairs" (Stoelting, sizes 2.36 (0.023 g), 2.44 (0.028 g) and 2.83 (0.068 g)) in dermatomes adjacent to the lesion. The allodynic responses were scored from 0 to 3 in a double blind manner and mean values determined for each time point of testing. Scoring was performed as follows: 0-no response; 1-transient flexing; 2-shaking; 3-escape.

1.8 Statistical Analysis

Differences in cell numbers were tested by Wilcoxon Rank Sum Test. The outcome values of the different tasks of the two treatment and the two control groups were compared statistically against each other at each time point using the Wilcoxon Rank Sum (Mann-Whitney U) test. The evolution of these outcome values was described separately in each group for BBB-, rotarod- and gridwalk-task, by the slope of the linear regression of the outcome value on time. An F-test was used to compare the slopes of the different groups. Animals showing no improvement had to be excluded in this parametric regression. To include all animals, we used the non-parametric procedure of Koziol (37) to compare the complete sets of evolution curves between the groups. The Pearson correlation coefficient was used to describe the dependency between the outcome value of different tasks (BBB score, swimming score and grid walk test) and the distance to the epicenter of the lesion, together with a statistical test on the presence of a non-zero correlation. Statistical significance was assessed on the level of 0.05 and reported by the p-value of the statistical test procedures. All analyses were performed with the program package ADAM of the Biostatistics Unit of the German Cancer Research Center.

2. Results

The dorsal two thirds of the spinal cord were transected in wt mice and the extent and temporal kinetic of apoptotic cell death were examined. Dead cells, as assessed by TUNEL staining, were detected at the lesion site already at day one after SCI, reaching maximal levels at 3 days to become barely detectable at 2 weeks (FIG. 1A). Importantly, CD95L expression kinetic paralleled apoptotic cell death (FIG. 1B). CD95 was already detectable in uninjured spinal cord, but additional CD95-positive cells were found after SCI (FIG. 1C). Expression of TNF increased at day one, peaking at day 3, and remained unchanged at 2 weeks (FIG. 1D). To dissect the contribution of the CD95- and the TNF-L/R systems to SCI-induced death, we neutralized the activity of CD95L and/or TNF. Tissue penetration of the neutralizing antibodies was confirmed by the detection of a biotinylated antibody in the injured spinal cord already at 3 h, and at 6 h and 24 h after i.p. injection (data not shown). Thereafter, the anti-CD95L and/or anti-TNF antibody (50 μg each) were i.p. injected in a double blind manner. In addition, the mice were injected with saline and rat IgG (50 μg) as a control. After survival time of 3 days, numerous TUNEL-positive cells were detected at the lesion site of saline- and IgG-treated animals (FIG. 1E). Acute neutralization of TNF did not significantly reduce cell death (FIG. 1E). Importantly, neutralization of CD95L alone or together with TNF, significantly decreased the number of TUNEL positive cells (FIG. 1E).

To investigate the long-term consequences of neutralization of CD95L and TNF, the locomotor performance and the reaction to mechanical stimulation of the injured mice were tested. For this, the animals were treated either with neutralizing antibodies against CD95L alone or together with TNF, or with saline or rat IgG twice a week up to four weeks (n=11 per group). All behavioural tests were performed in a double blind manner. Animals were evaluated before, and at one day (only for BBB locomotor test), 1, 2, 3 and 4 weeks after the injury. For all the tasks tested no statistically significant differences were found either between the two control groups, or between the two treated groups for any of the time points studied (Wilcoxon Rank Sum).

First, we quantified multiple aspects of spontaneous overground locomotion by BBB locomotor score (12). At day one after injury, all animals were completely paraplegic and had BBB score 0 (except for two animals that reached score 3; FIG. 2A). Animals in control groups exhibited no or only insignificant recovery of active movements throughout the studied time period (Koziol test). Most notably, the clinical evolution and the locomotor performance at each time point tested in mice in which CD95L, or both CD95L and TNF were blocked were significantly better than in control animals (FIG. 2A). Accordingly, the absolute locomotor recovery of the two treatment groups, as assessed by the slope of the linear regression analysis, was significantly better than in the control groups (FIG. 2A).

One of the limitations of the BBB score is that it focuses mainly on stereotyped movements controlled by reflex pathways in the spinal cord (i.e. central pattern generator) (13). Therefore, additional tests that reflect the integrity of dorsal spinal motor tracts (cortico- or rubrospinal tract) were performed. One of the tests that focuses on voluntary aspects of limb movements, is the grid walk test. Deficits in descending motor control were examined by assessing the ability to precisely control and place the hindpaws on a horizontal, ladder-like grid. Again, the only animals exhibiting a significant recovery of voluntary movements were the anti-CD95L- and anti-CD95L/anti-TNF-treated animals (FIG. 2B).

In order to obtain information about locomotor performance in the absence of the cutaneous and proprioceptive input from the limbs to the spinal cord, we used a swimming test. We evaluated the swimming performance by scoring from 0 to 10 the following features: hindlimb movements, hindlimb-forelimb coordination, tail position, paw position, saggital and coronal balance (Table 1). Once again, the mice treated with anti-CD95L- or anti-CD95L/anti-TNF-antibodies, showed a significant increase in the swimming score at every time point tested in comparison to saline- and IgG-treated animals (FIG. 2C).

To test motor coordination and skill-learning, rotarod test was performed (14). The maintenance time on a plastic roller that was accelerated from 4-7 r.p.m., was recorded. The time on the rotarod of animals treated with anti-CD95L was significantly longer at 2 and 3 weeks after SCI, and in anti-CD95L/anti-TNF-treated animals at 1, 3 and 4 weeks after SCI, when compared to control mice (FIG. 2D).

The enhanced voluntary movements of anti-CD95L- and anti-CD95L/anti-TNF-treated animals indicate an increased regenerative capacity of injured axons. However, this can be a double edged sword since aberrant sprouting can give rise to hyperalgesia (15). Neutralization of TNF attenuates hyperalgesia in mice with chronic constriction injury (16). To test the influence of neutralization of CD95L alone or together with TNF in the reaction of injured animals to otherwise nonnociceptive stimuli, we used the "von Frey test" (17). For this, the mice were tested for responses to low threshold mechanical stimulation by "von Frey hairs". The allodynic responses were scored from 0 to 3 depending on the intensity of the reaction to the stimulus. Preoperatively, all animals had an allodynic score of 0. At every time point after injury, only the double-treated mice showed a significant decrease in allodynic behavior when compared to control mice (FIG. 2E). Thus, a possible advantage of adding anti-TNF antibody to the treatment, could be to attenuate hyperalgesia.

To confirm the "placebo-like" effect of neutralization of TNF in the locomotor performance observed previously, a second set of experiments was performed. For this, animals were injected either with the anti-TNF antibody alone or with saline. As expected, the differences in the motor tasks as assessed by BBB (FIG. 2A) and grid walk (FIG. 2B) were not significant. However, the rotarod performance of the anti-TNF-treated animals was significantly better in comparison to saline treated mice (FIG. 2D). Along this line, brain-injured TNF knock-out mice were significantly less impaired in rotarod test and had significantly less severe deficits in memory retention than wt mice (18). In accordance with previous reports, only anti-TNF-, but not saline-treated animals exhibited a significant decrease of the allodynic reaction throughout the time period studied (linear regression analysis, data not shown).

The integrity of the dorsal corticospinal tract (CST) in some of the previously tested animals (4-5 per group), was assessed by injection of biotin-dextran amine (BDA) into the sensory-motor cortex (19). In mice receiving saline or IgG, transected CST fibers retracted from the lesion site by ~250 µm (±11.5 µm) (FIG. 3A). Only the few sprouts that extended from the cut axons to the adjacent tissue were detected, but they did not grow into the lesion area. Significantly, in anti-CD95L- or anti-CD95L/anti-TNF-treated animals, numerous ectopic fibers sprouted from the transsected CST rostral to the lesion site (FIG. 3B). These regenerating fibers grew into the dorsal white matter and lesion scar. Few fibers even crossed the lesion epicenter. The relatively low number of crossing fibers compared to other studies (20) is related to the size of the injury. Here, we cut two thirds of spinal cord which leads to the transsection of the whole dorsal component of CST. Accordingly, large spinal cord lesions correlate with poor regenerative growth (20). High magnification views of CST fibers at the lesion site of anti-CD95L- and anti CD95L/anti-TNF-treated animals demonstrated a morphology consistent with synaptic buttons, suggesting that functional connections are formed by these regenerating fibers (FIG. 3B).

Interestingly, despite of the low number of BDA-traced animals, it was evident from the data that fiber regeneration correlated with the score in the grid walk performance (R=0.66; p≦0.05; Pearson correlation). This score reflects voluntary movements, and therefore, the functional improvement of the anti-CD95L- and anti-CD95L/anti-TNF-treated animals can not be due to spared ventral tracts (reticulo- and vestibulo-spinal tracts) that are in charge of producing reflex movements.

To figure out the molecular mechanisms behind the clinical recovery of the animals, the expression of various markers for degeneration, regeneration or inflammation was assessed. Proteins were extracted from the spinal cords of animals (n=3 per group) previously tested for locomotor performance.

We know that neutralization of CD95L decreases apoptosis. But, which cell types are rescued? Neurons and microglia express both CD95L and CD95, astrocytes express TNF and CD95, whereas infiltrating lymphocytes express CD95L (data not shown). In contrast to astrocytes, oligodendrocytes are susceptible to CD95-induced apoptosis (21). Since CD95 is also expressed in neurons and microglia, rescued cells must be either neurons, microglia or oligodendrocytes.

To address this issue, expression of a neuronal cytoskeletal protein, βIII-tubulin was assessed (22). The level of βIII-tubulin has been shown to increase during axonal regeneration (23). Accordingly, in animals treated with anti-CD95L- or anti-CD95L/anti-TNF, but not in control groups, βlll-Tubulin expression was markedly increased (FIG. 4A).

Further, we examined the expression of Tau, a neuronal microtubule associated protein. As expected, the total amount of Tau, as assessed by Tau5 antibody, was higher in both treated groups (FIG. 4A). Most importantly, the proportion of non-phosphorylated Tau (Ser 199 and 202) was higher in the treated groups (FIG. 4A). Moreover, in anti-CD95L- and anti-CD95L/anti-TNF-treated animals, one additional band was detected for Tau (arrows). To determine if this band was due to degradation or dephosphorylation of Tau, we treated the lysates with alkaline phosphatase (AP). Treatment with AP shifted the upper bands down (data not shown). Thus, we conclude that neutralization of CD95L facilitates Tau dephosphorylation. Dephosphorylated Tau stabilizes microtuble (MT) structures, therefore allowing for axonal growth (24).

It has been reported that oligodendrocytes undergo apoptosis following SCI (25). The loss of oligodendrocytes results in demyelination of axons that might have survived the initial trauma. Moreover, the CD95-L/R system has been postulated as a major trigger of demyelination in multiple sclerosis (26). It is therefore tempting to speculate that treatment with anti-CD95L decreases oligodendrocyte death and, thus, axonal demyelination following spinal cord injury. To address this issue we assessed the levels of the Myelin basic protein (MBP). This protein is made by oligodendrocytes and its presence can serve as an indirect parameter of oligodendrocyte viability (27). In animals treated with anti-CD95L alone or together with anti-TNF, MBP levels increased compared to control mice (FIG. 4B).

Regeneration can also be facilitated by interfering with the inflammatory response. Amplification of the inflammatory reaction can be driven by CD95L and TNF, as is the case in other systems (28). Following SCI, reactive astrocytes invade the lesion site to produce the astroglial scar. The scar becomes a mechanical obstacle for axonal regeneration (29). Inhibition of CD95L might reduce scar formation following SCI. Therefore, we assessed the levels of the marker for reactive astrocytes, the Glial fibrillary acidic protein (GFAP). Expression levels of GFAP did not differ between treated, and controlgroups (FIG. 4C).

Neutralization of CD95L could also directly increase the regeneration potential of injured axons. To test this, we examined the expression levels of Growth-associated-protein 43 (GAP-43). Expression of GAP-43 has been shown to increase after thoracic SCI only in axons that can regenerate (30). Moreover, co-expression of GAP-43 and CAP-23, another major growth cone protein, leads to 60-fold increase in regeneration of DRG axons after SCI (31). In anti-CD95L- and anti-CD95L/anti-TNF-treated animals, GAP-43 expression increased when compared to control groups (FIG. 4D).

In summary, first we have shown with locomotor tests that neutralization of CD95L promotes functional recovery following SCI. Apart from the BBB score that focuses mainly on stereotyped, reflex movements, we also performed tests that reflect the integrity of dorsal spinal tracts that are affected by lesioning. These are the grid walk test an the swimming test. We developed a swimming scale according to the swimming performance of the animals in order to quantify the multiple aspects of locomotion in the absence of the cutaneous and proprioceptive input from the limbs to the spinal cord. In every test, the functional recovery of the anti-CD95L- and the anti-CD95L/anti-TNF-treated animals was significantly better than in the two control groups. Animals treated with anti-TNF alone did not exhibit significant functional recovery, but addition of anti-TNF antibody to the treatment attenuated mechanical allodynia.

Second, the BDA-tracing study indicated an increased regenerative capacity of injured axons only in anti-CD95L- and anti-CD95L/anti-TNF-treated animals. Moreover, these regenerating fibers formed functional connections, as demonstrated by formation of synaptic buttons at the lesion site. Thus, neutralization of CD95L is likely to enhance axonal plasticity, leading to the functional remodelling of spinal cord circuitry. Axonal regeneration occurred despite the lack of a CD95L effect on the scar of the lesion. The locomotor recovery and increased regeneration were mirrored by an increase of the neuronal marker βIII-tubulin, as well as by an increase in oligodendrocyte viability. Therefore, neutralization of CD95L both protects neurons and inhibits demyelination. Moreover, GAP-43 expression increased in anti-CD95L- and anti-CD95L/anti-TNF-treated animals, indicating that neutralization of CD95L might directly increase the regenerative potential of injured axons. Also, GAP-43 can increase because maintenance of oligodendrocyte viability prevents axonal demyelination and gives axons the possibility to regenerate.

The spinal and cerebral trauma account for the majority of cases of death and permanent disabilities in the population under the age of 40. The consequences for the society are devastating, having been coined as the silent epidemy. Currently, the strategies aimed at repairing spinal cord lesions focus either on neuroprotection, enhanced regeneration, or treatment of demyelination. Given the complexity of spinal cord injury, multiple interventions targeting the different sources of damage would be required. We demonstrated that following SCI, neutralization of CD95L acts on three levels: it protects neurons, inhibits demyelination, and promotes regeneration and, therefore, may offer a new therapy for human spinal trauma.

EXAMPLE 2

Treatment of Spinal Cord Injury with a CD95-Fc Fusion Protein

We tested whether a CD95-Fc fusion protein (e.g. as disclosed in WO 95/27735) is capable of exerting a therapeutic effect following SCI by hemisection. The test animals (n=6) were intraperitonally treated seven times with 25 mg/kg CD95-Fc each third day, respectively. The control animals (n=6) were treated with saline. Indeed, repeated administration of CD95-Fc significantly attenuated hind limb paralysis of mice four weeks following spinal hemisection. The results are shown in FIG. 6. CD95-Fc-treated mice recovered hind limb motility to a BBB-score of 11 in average. This score corresponds to full weight support and a mostly plantar placement of hind limbs. Saline-treated mice in contrast, had an average score of 1.5 which corresponds to a slight movement ability of hind limbs at two joints but otherwise a disability to use hind limbs for locomotion.

Treatment with CD95-Fc effectively ameliorated functional recovery of hind limb movement following cervical spinal hemisection. A progress of hind limb motility as demonstrated here in mice would correspond to a drastic improvement of quality of life and a reduced need for health care when correlated to humans suffering from paralysis following SCI.

TABLE 1

| PAW POSITION | | MOVEMENT >ONE JOINT | | | | | | HL-FL COORDINATION | | | BALANCE around Z-axe | | TAIL | |
|---|---|---|---|---|---|---|---|---|---|---|---|---|---|---|
| 90° Paralell to trunk | Paralell to trunk | ONE JOINT NO | slight | Ext. ext | X-Balance slight | no | yes | No | Occass.. | Consist. | No | Yes | DOWN | UP |
| 0 | 1 | 0 | 1 | 2 | 3 | 4 | 5 | 0 | 1 | 2 | 0 | 1 | 0 | 1 |

REFERENCES (1) M. J. Crowe, J. C. Bresnahan, S. L. Shuman, J. N. Masters, M. S. Beattie, Nat Med 3, 73-6. (1997).
(2) A. Martin-Villalba et al., Cell Death Differ 8, 679-86. (2001).
(3) L. A. Tartaglia, T. M. Ayres, G. H. Wong, D. V. Goeddel, Cell 74, 845-53. (1993).
(4) F. C. Kischkel et al., Embo J 14, 5579-88. (1995).
(5) J. P. Medema et al., Embo J 16, 2794-804. (1997).
(6) C. Scaffidi et al., Embo 17, 1675-87. (1998).
(7) J. E. Springer, R. D. Azbill, P. E. Knapp, Nat Med 5, 943-6. (1999).
(8) M. Li et al., Neuroscience 99, 333-42. (2000); M. Zurita, J. Vaquero, I. Zurita, J Neurosurg 94, 257-64. (2001).
(9) Y. B. Lee et al., Exp Neurol 166, 190-5. (2000).
(10) G. M. Kim et al., J Neurosci 21, 6617-25. (2001); M. Farooque, J. Isaksson, Y. Olsson, J Neurotrauma 18, 105-14. (2001).
(11) S. Casha, W. R. Yu, M. G. Fehlings, Neuroscience 103, 203-18. (2001).
(12) D. M. Basso, M. S. Beattie, J. C. Bresnahan, J Neurotrauma 12, 1-21. (1995).
(13) S. Rossignol, R. Dubuc, Curr Opin Neurobiol 4, 894-902. (1994).
(14) L. L. Counghenour, J. R. McLean, R. B. Parker, Pharmacol Biochem Behav 6, 351-3. (1977).
(15) C. J. Woolf, Drugs 47, 1-9, discussion 46-7. (1994).
(16) T. Lindenlaub, P. Teuteberg, T. Hartung, C. Sommer, Brain Res 866, 15-22. (2000).
(17) A. E. Lindsey et al., Neurorehabil Neural Repair 14, 287-300. (2000).
(18) U. Scherbel et al., Proc Natl Acad Sci USA 96, 8721-6. (1999).
(19) J. D. Guest et al., J Neurosci Res 50, 888-905. (1997).
(20) C. Brosamle, A. B. Huber, M. Fiedler, A. Skerra, M. E. Schwab, J Neurosci 20, 8061-8. (2000); T. GrandPre, S. Li, S. M. Strittmatter, nature 417, 547-51. (2002).
(21) S. D. D'Souza et al., J Exp Med 184, 2361-70. (1996); B. Becher, S. D. D'Souza, A. B. Troutt, J. P. Antel, Neuroscience 84, 627-34. (1998); W. Li et al., J Neurosci Res 69, 189-96. (2002).
(22) H. Braun, K. Schafer, V. Hollt, J Neurotrauma 19, 975-83. (2002).
(23) A. E. Fournier, L. McKerracher, J Neurosci 17, 4623-32. (1997).
(24) D. A. Shackelford, K. E. Nelson, J Neurochem 66, 286-95. (1996).
(25) S. L. Shuman, J. C. Bresnahan, M. S. Beattie, J Neurosci Res 50, 798-808. (1997).
(26) U. Malipiero et al., Eur J Immunol 27, 3151-60. (1997).
(27) D. Bartholdi, M. E. Schwab, Glia 23, 278-84. (1998).
(28) J. J. Chen, Y. Sun, G. J. Nabel, Science 282, 1714-7. (1998); Y. Mano-Hirano et al., J Natl Cancer Inst 78, 115-20. (1987).
(29) S. J. Davies et al., Nature 390, 680-3. (1997).
(30) K. J. Fernandes, D. P. Fan, B. J. Tsui, S. L. Cassar, W. Tetzlaff, J Comp Neurol 414, 495-510. (1999).
(31) H. M. Bomze, K. R. Bulsara, B. J. Iskandar, P. Caroni, J. H. Skene, Nat Neurosci 4, 38-43. (2001).
(32) B. Echtenacher, W. Falk, D. N. Mannel, P. H. Krammer, J Immunol 145, 3762-6. (1990).
(33) Y. Gavrieli, Y. Sherman, S. A. Ben-Sasson, J Cell Biol 119, 493-501. (1992).
(34) A. Herzog, C. Brosamle, J Neurosci Methods 72, 57-63. (1997).
(35) D. M. Basso, M. S. Beattie, J. C. Bresnahan, J Neurotrauma 12, 1-21. (1995).
(36) G. A. Metz, D. Merkler, V. Dietz, M. E. Schwab, K. Fouad, Brain Res 883, 165-77. (2000).
(37) J. A. Koziol, D. A. Maxwell, M. Fukushima, M. E. Colmerauer, Y. H. Pilche, Biometrics 37, 383-90. (1981).
(38) N. Kayagaki et al., Proc. Natl. Acad. Sci USA 94, 3914. (1997).
(39) Y. Nakamoto et al., J. Exp. Med. 196, 1105. (2002).
(40) B. Echtenacher et al., J Immunol 145, 3762-3766. (1991).
(41) V. J. Wroblewski et al., Biochem Pharmacol 65, 657-667. (2003).
(42) M. Zurita et al., J. Neurosurg. (Spine 2) 94, 257-264. (2001).
(43) B. Becker et al., Neuroscience 84, 627-634. (1998).
(44) M. Farooque et al., J. Neurotrauma 18, 105-114. (2001).

The invention claimed is:

1. A method for treating cerebral or spinal cord injury comprising administering to a human in need thereof, a therapeutically effective amount of an inhibitor of CD95 receptor/ligand system, wherein said inhibitor is
   (a) an inhibitory anti-CD95 ligand-antibody or an antigen-binding fragment thereof; or
   (b) a soluble CD95 receptor molecule or a CD95 ligand binding portion thereof and wherein said inhibitor of CD95 receptor/ligand system is administered without a TNF L/R inhibitor.

2. The method according to claim 1, comprising treating partial or complete spinal cord lesions.

3. The method according to claim 1, comprising treating paraplegia.

4. A method for the regeneration of locomotor performance, improvement of reactions to stimulation or recovery of movement coordination following cerebral or spinal cord injury in a human in need thereof comprising administering to said human a therapeutically effective amount of an inhibitor of CD95 receptor/ligand system, wherein said inhibitor is
   (a) an inhibitory anti-CD95 ligand-antibody or an antigen-binding fragment thereof; or (b) a soluble CD95 receptor molecule or a CD95 ligand binding portion thereof;
and wherein said inhibitor of CD95 receptor/ligand system is administered without a TNF L/R inhibitor.

5. The method according to claim 1, wherein the subject is an adult subject.

6. The method according to claim 1, wherein the CD95 ligand inhibitor is an extracellular domain of the CD95 receptor molecule optionally fused to a heterologous polypeptide domain.

7. The method according to claim 1, wherein the CD95 ligand inhibitor is an extracellular domain of the CD95 receptor molecule fused to a Fc immunoglobulin molecule.

8. The method according to claim 1 wherein the inhibitor is an inhibitory anti-CD95 ligand-antibody or a fragment thereof.

9. The method according to claim 1, comprising administering a medicament which comprises at least one said inhibitor as the active ingredient together with pharmaceutically acceptable carrier, diluent or adjuvant.

10. The method according to claim 9 wherein the medicament is administered systemically.

11. The method according to claim 9 wherein the medicament is administered locally.

12. The method according to claim 9 wherein the medicament is administered intrathecally.

13. The method according to claim 1, comprising treating an acute injury.

14. The method according to claim 1, comprising treating a non-acute injury after introduction of a new damage.

15. The method according to claim 9, wherein the medicament comprises a further active ingredient.

16. The method according to claim 15 wherein the further active ingredient is an apoptosis inhibitor which is a caspase-3 inhibitor, a caspase-8 inhibitor, a Bid inhibitor, a Bax inhibitor or a combination thereof.

17. The method according to claim 15 wherein the further active ingredient is an inhibitor of a death ligand/receptor system wherein said death ligand/receptor ligand system is a TRAIL/L TRAIL-R system, a TRAMP-L/TRAMP-R system, or a DR6-L/DR6-R system.

18. The method according to claim 15 wherein the further active ingredient is chondroitinase ABC.

19. The method according to claim 1, wherein the cerebral or spinal cord injury is due to a cut.

20. The method according to claim 1, wherein the cerebral or spinal cord injury is due to compression of said spinal cord.

21. The method according to claim 1, wherein the cerebral or spinal cord injury is non-ischemic cerebral or spinal cord injury.

\* \* \* \* \*